(12) United States Patent
Kitanaka

(10) Patent No.: US 11,596,294 B2
(45) Date of Patent: Mar. 7, 2023

(54) VARIABLE STIFFNESS DEVICE AND METHOD OF VARYING STIFFNESS

(71) Applicant: OLYMPUS CORPORATION, Tokyo (JP)

(72) Inventor: Tomohiro Kitanaka, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 777 days.

(21) Appl. No.: 16/597,066

(22) Filed: Oct. 9, 2019

(65) Prior Publication Data

US 2020/0037853 A1 Feb. 6, 2020

Related U.S. Application Data

(63) Continuation of application No. PCT/JP2017/015320, filed on Apr. 14, 2017.

(51) Int. Cl.
*G08B 21/04* (2006.01)
*A61B 1/00* (2006.01)

(52) U.S. Cl.
CPC . *A61B 1/00078* (2013.01); *A61M 2205/0266* (2013.01)

(58) Field of Classification Search
USPC ........ 340/539.12, 539.1, 539.27, 545.6, 551, 340/568.8, 622, 636.18, 636.17, 640, 655
See application file for complete search history.

(56) References Cited

U.S. PATENT DOCUMENTS 6,779,602 B1 * 8/2004 Van Bilderbeek ...... E21B 33/10
166/216
2008/0302418 A1 * 12/2008 Buller ............. H01L 31/035281
136/265
(Continued)

FOREIGN PATENT DOCUMENTS

| JP | 2006-334201 A | 12/2006 |
| WO | WO 2016/121060 A1 | 8/2016 |
| WO | WO 2016/174741 A1 | 11/2016 |

OTHER PUBLICATIONS

English translation of International Preliminary Report on Patentability dated Oct. 24, 2019, together with the Written Opinion received in related International Application No. PCT/JP2017/015320.
(Continued)

*Primary Examiner* — Daniel Previl
(74) *Attorney, Agent, or Firm* — Scully, Scott, Murphy & Presser, P.C.

(57) ABSTRACT

A variable stiffness device includes a first elongated member in a hollow shape extending along a longitudinal axis, and a second elongated member including a heater, disposed inside an inner circumference of the first elongated member, and extending in parallel to the first elongated member along the longitudinal axis. The first elongated member includes a high bending stiffness portion and a low bending stiffness portion alternately aligned along the longitudinal axis. One of the first elongated member and the second elongated member includes a shape-memory pipe. The heater extends through an inner space of the shape-memory pipe and configured to heat the shape-memory pipe to increase stiffness of the shape-memory pipe.

18 Claims, 13 Drawing Sheets

(56) References Cited

U.S. PATENT DOCUMENTS

| | | | | |
|---|---|---|---|---|
| 2012/0234468 A1* | 9/2012 | Pitman | ...................... | B32B 5/02 |
| | | | | 156/185 |
| 2014/0301674 A1* | 10/2014 | Sanfilippo | .......... | B65D 75/5838 |
| | | | | 383/84 |
| 2015/0148791 A1* | 5/2015 | Birdsall | ................. | A61B 18/02 |
| | | | | 606/22 |
| 2017/0321666 A1* | 11/2017 | Morishima | ........ | A61B 1/00078 |

OTHER PUBLICATIONS

International Search Report dated Jun. 13, 2017 issued in PCT/JP2017/015320.

\* cited by examiner

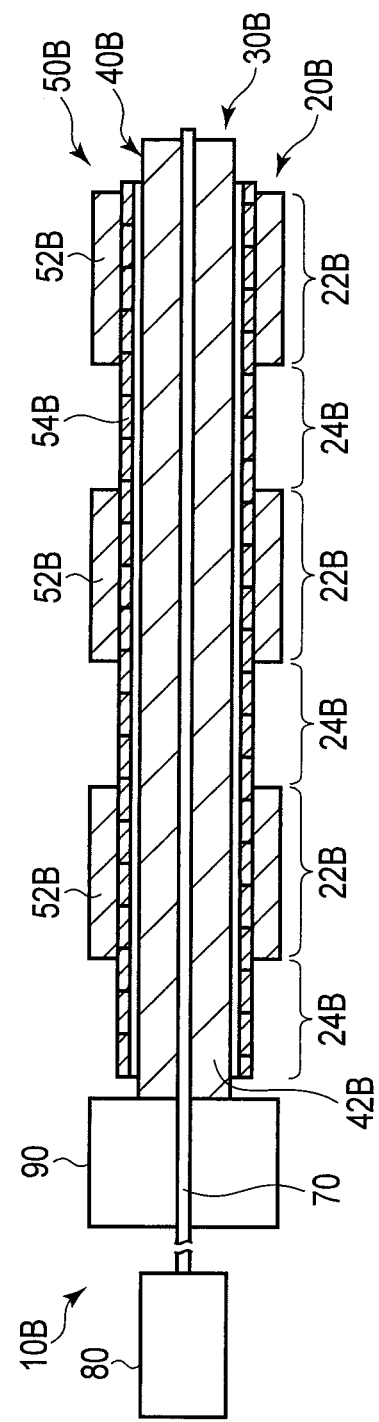
F I G. 3A

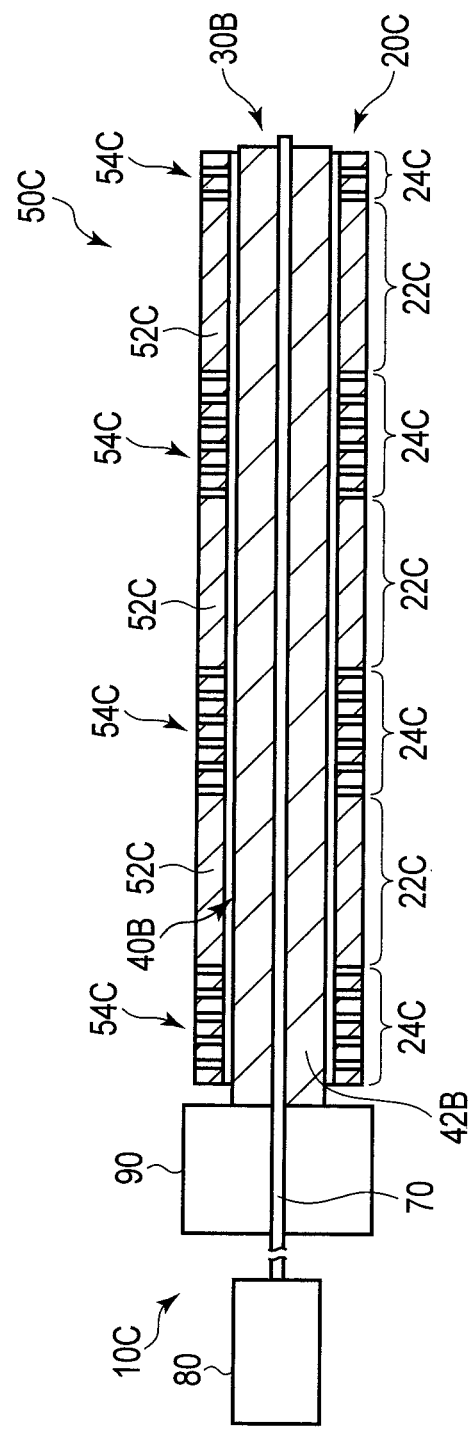
F I G. 4

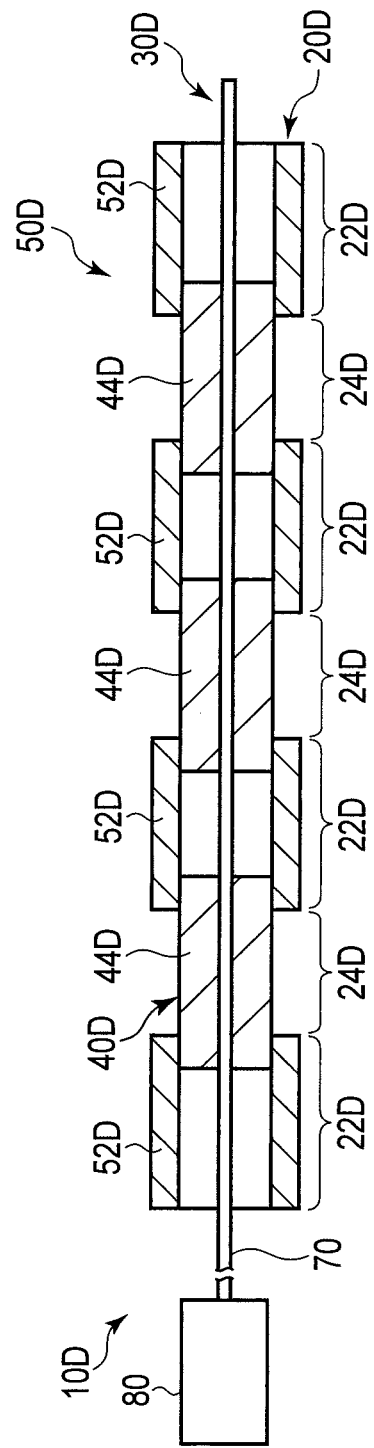
F I G. 5A

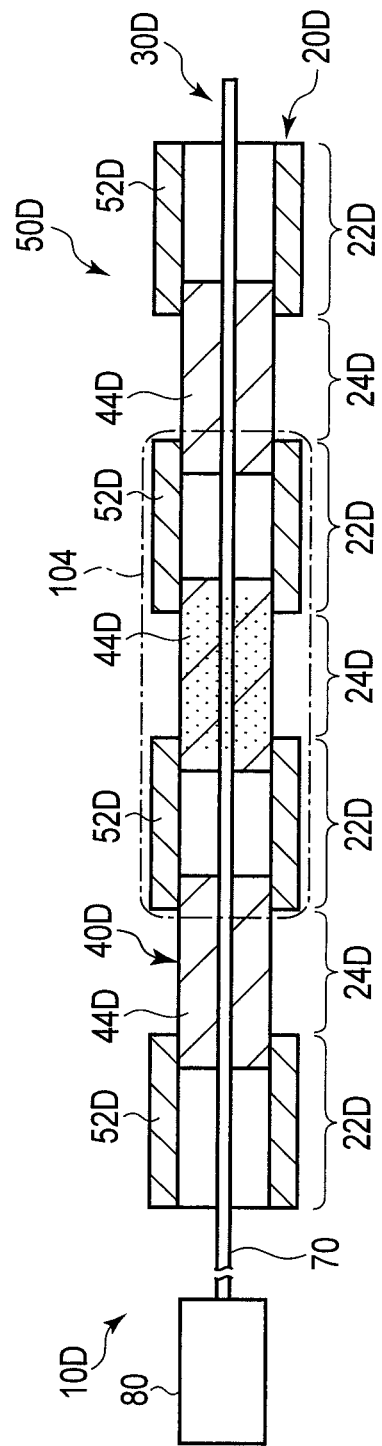
F I G. 5B

VARIABLE STIFFNESS DEVICE AND METHOD OF VARYING STIFFNESS

CROSS-REFERENCE TO RELATED APPLICATIONS

This application is a Continuation Application of PCT Application No. PCT/JP2017/015320, filed Apr. 14, 2017, the entire contents of which are incorporated herein by reference.

BACKGROUND OF THE INVENTION

1. Field of the Invention

The present invention relates to a variable stiffness device that provides different stiffness to a flexible member.

2. Description of the Related Art

For example, International Publication No. 2016/174741 discloses such a variable stiffness device. The variable stiffness device is to be installed in a flexible member, and is configured to provide different hardness to the flexible member. The variable stiffness device includes a shape-memory member that can transition in phase between the first phase and the second phase depending on temperature, and a heating element configured to cause the shape-memory member to transition in phase. When in the first phase, the shape-memory member takes a soft state in which the shape-memory member can be easily deformed according to an external force, providing relatively low stiffness to the flexible member. Also, when in the second phase, the shape-memory member takes a high stiffness state showing a tendency to take a memory shape memorized in advance against an external force, providing relatively high stiffness to the flexible member.

BRIEF SUMMARY OF THE INVENTION

An aspect of the invention is directed to a variable stiffness device. The variable stiffness device includes a first elongated member in a hollow shape extending along a longitudinal axis, and a second elongated member including a heater, disposed inside an inner circumference of the first elongated member, and extending in parallel to the first elongated member along the longitudinal axis. The first elongated member includes a high bending stiffness portion and a low bending stiffness portion alternately aligned along the longitudinal axis. One of the first elongated member and the second elongated member includes a shape-memory pipe. The heater extends through an inner space of the shape-memory pipe and configured to heat the shape-memory pipe to increase stiffness of the shape-memory pipe.

Another aspect of the invention is directed to a method of varying stiffness of the variable stiffness device. The method includes heating the shape-memory pipe by the heater to increase bending stiffness of the shape-memory pipe, and lowering temperature of the shape-memory pipe to decrease the bending stiffness of the shape-memory pipe.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A shows a variable stiffness device according to a second embodiment.

FIG. 4 shows a variable stiffness device according to a modification of the second embodiment.

FIG. 5A shows a variable stiffness device according to a third embodiment.

FIG. 5B shows the variable stiffness device according to the third embodiment.

DETAILED DESCRIPTION OF THE INVENTION

First Embodiment

Configuration

Figure 1A:
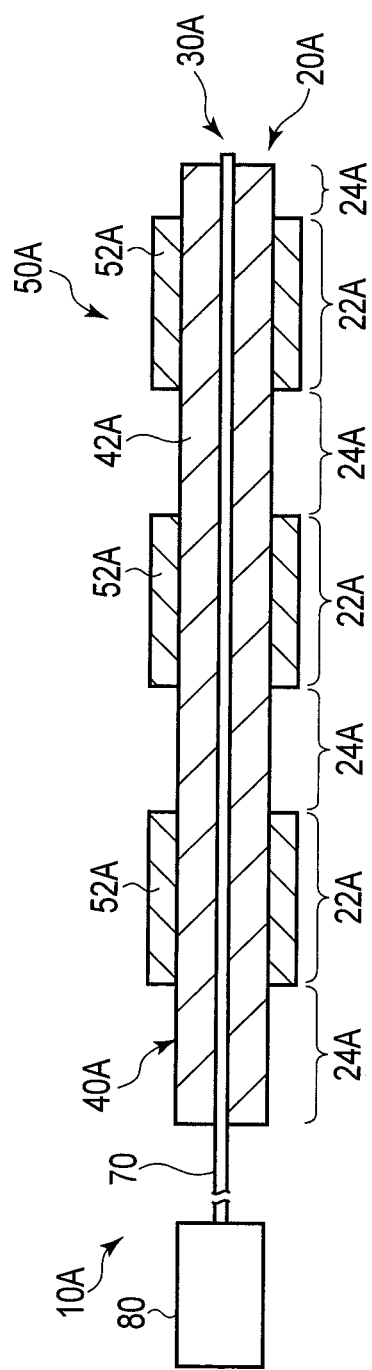
FIG. 1A shows a variable stiffness device according to a first embodiment.
Figure 1B:
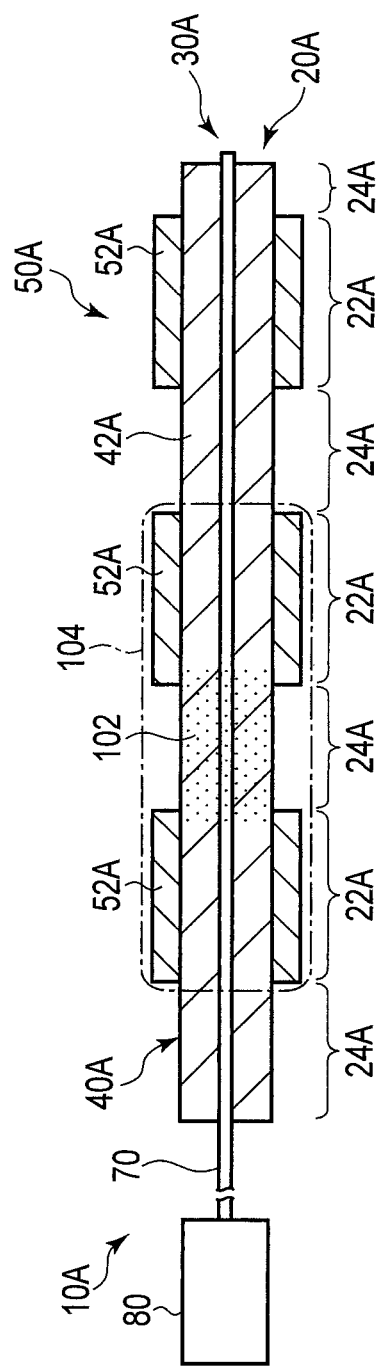
FIG. 1B shows the variable stiffness device according to the first embodiment.

FIGS. 1A and 1B show a variable stiffness device 10A according to a first embodiment. The variable stiffness device 10A is a device that is to be installed in a flexible member, which is an object to be installed, and is configured to provide partially different stiffness to the flexible member. The flexible member may be, for example, but is not limited to, an insertion section of an endoscope. FIG. 1A depicts the variable stiffness device 10A in a soft state that provides partially relatively low stiffness to the flexible member, and FIG. 1B depicts the variable stiffness device 10A in a hard state that provides relatively high stiffness to the flexible member.

As shown in FIGS. 1A and 1B, the variable stiffness device 10A includes a first elongated member 20A and a second elongated member 30A. The first elongated member 20A extends along a longitudinal axis. Similarly to the first elongated member 20A, the second elongated member 30A extends along the longitudinal axis, and is disposed along and adjacent to the first elongated member 20A. The first elongated member 20A and the second elongated member 30A are fixed to each other so that their relative position will not change.

The first elongated member 20A includes high bending stiffness portions 22A and low bending stiffness portions 24A. For example, the first elongated member 20A includes three high bending stiffness portions 22A and four low bending stiffness portions 24A. The high bending stiffness portions 22A and the low bending stiffness portions 24A are alternately arranged along the longitudinal axis of the first elongated member 20A. The high bending stiffness portion 22A has higher bending stiffness than that of the low bending stiffness portion 24A. For this reason, the first elongated member 20A is relatively easy to bend at the portion of the low bending stiffness portion 24A, and relatively difficult to bend at the portion of the high bending stiffness portion 22A.

The first elongated member 20A does not necessarily have to include high bending stiffness portions 22A and low bending stiffness portions 24A. The first elongated member 20A only needs to include at least one high bending stiffness portion 22A and at least one low bending stiffness portion 24A. For example, the first elongated member 20A may be a configuration including two high bending stiffness portions 22A and one low bending stiffness portion 24A.

The first elongated member 20A is constituted of a pipe 50A, and includes a shape-memory pipe 40A extending along the longitudinal axis. The shape-memory pipe 40A is constituted of a full length extending shape-memory pipe 42A continuously extending over substantially the entire length of the first elongated member 20A. The first elongated member 20A also includes a hard pipe 52A partially extending along the full length extending shape-memory pipe 42A around the full length extending shape-memory pipe 42A. For example, the first elongated member 20A includes hard pipes 52A extending spaced apart from one another along the full length extending shape-memory pipe 42A. A distance between the hard pipes 52A may or may not be constant. In other words, the pipe 50A is constituted of the full length extending shape-memory pipe 42A and the hard pipes 52A.

Herein, the full length extending shape-memory pipe 42A extending over substantially the entire length of the first elongated member 20A does not necessarily mean that the total length of the full length extending shape-memory pipe 42A is equal to that of the first elongated member 20A, and means that the case where the total length of the full length extending shape-memory pipe 42A is shorter than that of the first elongated member 20A is also included. For example, when a hard pipe 52A is located at an end of the first elongated member 20A, the total length of the full length extending shape-memory pipe 42A may be shorter than that of the first elongated member 20A. Such a configuration is also included in the meaning that the full length extending shape-memory pipe 42A extends over substantially the entire length of the first elongated member 20A.

The hard pipe 52A has higher stiffness than that of the full length extending shape-memory pipe 42A. The hard pipe 52A constitutes a part of the high bending stiffness portion 22A, and a part of the full length extending shape-memory pipe 42A constitutes the low bending stiffness portion 24A. Specifically, the hard pipe 52A constitutes the high bending stiffness portion 22A together with a covered portion of the full length extending shape-memory pipe 42A that is covered by the hard pipe 52A. An exposed portion of the full length extending shape-memory pipe 42A that is not covered by the hard pipe 52A constitutes the low bending stiffness portion 24A. The stiffness of the low bending stiffness portion 24A varies depending on the state of the phase of the full length extending shape-memory pipe 42A of that portion. Namely, the low bending stiffness portion 24A can be considered to be a variable bending stiffness portion. The low bending stiffness portion 24A has higher stiffness when the full length extending shape-memory pipe 42A of that portion is in the high stiffness state than when in the low stiffness state.

Each hard pipe 52A is constituted of, for example, a pipe of SUS (stainless steel). Each hard pipe 52A is preferably made of a material having good thermal conductivity. Each hard pipe 52A is fixed to the full length extending shape-memory pipe 42A. Fixing of each hard pipe 52A to the full length extending shape-memory pipe 42A may be performed, for example, by brazing or caulking.

The shape-memory pipe 40A has a property that the phase can transition between the first phase and the second phase, i.e., causing phase transformation, depending on a change in temperature.

When in the first phase, the shape-memory pipe 40A takes the low stiffness state, i.e., exhibits a low elastic modulus, thus providing relatively low stiffness to the flexible member. When in the first phase, the shape-memory pipe 40A can be easily deformed according to an external force.

When in the second phase, the shape-memory pipe 40A takes the high stiffness state, which is a state with higher stiffness than when in the low stiffness state, i.e., exhibits a high elastic modulus, thus providing relatively high stiffness to the flexible member. When in the second phase, the shape-memory pipe 40A tends to take a memory shape memorized in advance, against an external force. The memory shape of the shape-memory pipe 40A is, for example, but is not limited to, a linear shape.

The shape-memory pipe 40A is easily deformed according to the external force in the low stiffness state, and tends to return to the memory shape memorized in advance against the external force in the high stiffness state. Herein, the external force means a force that can cause the shape-memory pipe 40A to deform, and gravity is considered to be a part of the external force.

The shape-memory pipe 40A has, for example, a cylindrical shape. In this case, the shape-memory pipe 40A provides the same bending stiffness for bending in any direction. The shape-memory pipe 40A does not necessarily have to have a cylindrical shape, and may have another shape.

The shape-memory pipe 40A is made of, for example, a shape-memory alloy. The shape-memory alloy may be, for example, but is not limited to, an alloy including NiTi. The shape-memory alloy is preferably NiTiCu having a large change in stiffness before and after the phase transition, but of course, any shape-memory alloy whose stiffness changes depending on the temperature change may be used.

For example, the shape-memory alloy may be what transitions in phase between a martensitic phase and an austenitic phase. The shape-memory alloy plastically deforms relatively easily with respect to the external force when in the martensitic phase. Namely, the shape-memory alloy exhibits a low elastic modulus when in the martensitic phase. On the other hand, when in the austenitic phase, the shape-memory alloy resists the external force and is not easily deformed. Even if the shape-memory alloy is deformed due to a larger external force, if the large external force disappears, it exhibits superelasticity and returns to the memory shape. Namely, the shape-memory alloy exhibits a high elastic modulus when in the austenitic phase.

Furthermore, the shape-memory alloy has a property of causing stress-induced martensitic transformation. Namely, the shape-memory alloy has a property that the phase transitions from the austenitic phase to the martensitic phase under stress.

The second elongated member 30A includes a heater 70 extending through an inner space of the shape-memory pipe 40A. The heater 70 is fixed to the shape-memory pipe 40A so that a relative positional relationship with the shape-memory pipe 40A will not change.

The heater 70 has a function of causing the shape-memory pipe 40A to transition in phase between the first phase and the second phase. Specifically, the heater 70 is configured to receive a supply of current and then generate heat to cause a phase transition from the first phase to the second phase in the full length extending shape-memory pipe 42A. The full length extending shape-memory pipe 42A has a property that the phase transitions from the first phase to the second phase by being heated by heat generation of the heater 70.

The heater 70 is electrically connected to a current supply unit 80 configured to supply a current to the heater 70. In other words, the variable stiffness device 10A includes the current supply unit 80 configured to supply a current to the heater 70.

Figure 2:
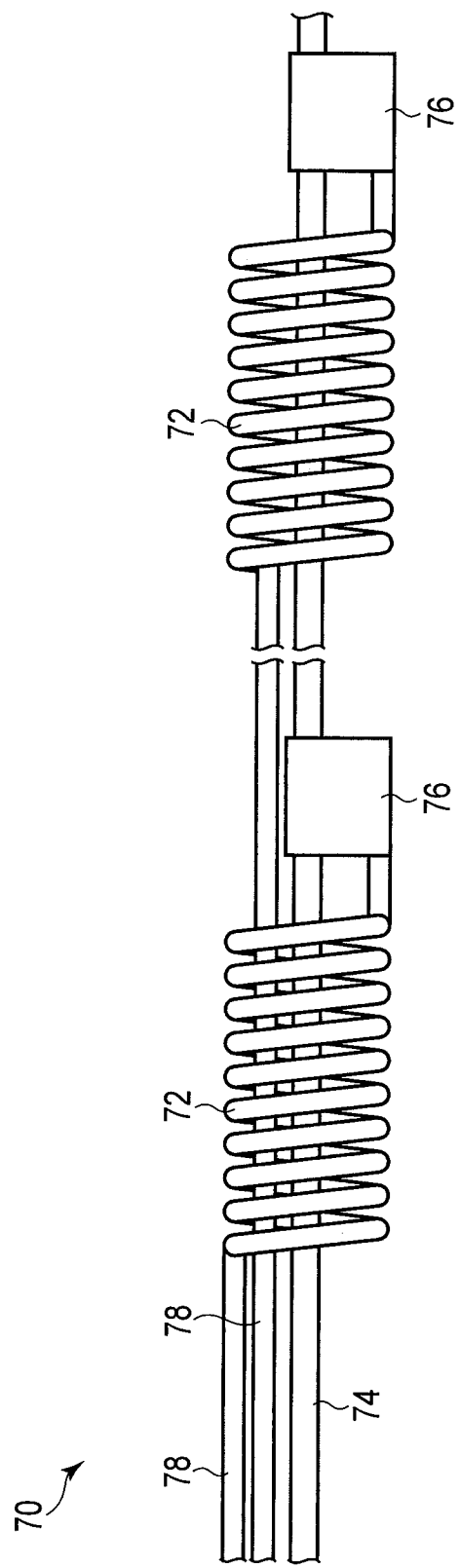
FIG. 2 shows an enlarged part of a heater shown in FIG. 1.

FIG. 2 shows a part of the heater 70 in an enlarged manner. The heater 70 comprises heating elements 72 spaced apart from one another along the longitudinal axis. Ends of the heating elements 72 are electrically connected in common to a conducting wire 74 extending along the longitudinal axis through connecting members 76. The other ends of the heating elements 72 are electrically connected to lead wires 78. The heating element 72 is constituted of, for example, a coil heater extending helically around the conducting wire 74 and the lead wire 78. The conducting wire 74 and the lead wire 78 are both electrically connected to the current supply unit 80 in order to supply a current to the heating element 72. With such a configuration, supplying a current from the current supply unit 80 to between one of the lead wires 78 and the conducting wire 74 allows the heating element 72 connected to that lead wire 78 to independently heat.

The heater 70 does not necessarily have to include heating elements 72. As described above, the first elongated member 20A only needs to include at least one high bending stiffness portion 22A and at least one low bending stiffness portion 24A. In this case, the heater 70 only needs to include at least one heating element 72.

Although not shown in FIGS. 1A and 1B, the heating element 72 is disposed between adjacent two of the hard pipes 52A spaced apart from one another along the longitudinal axis. Namely, the heating element 72 has a function of heating the portion of the full length extending shape-memory pipe 42A between adjacent two of the high bending stiffness portions 22A. In other words, the heating element 72 has a function of heating the portion of the full length extending shape-memory pipe 42A that is disposed at a position corresponding to the low bending stiffness portion 24A and constitutes the low bending stiffness portion 24A.

On the other hand, the heating element 72 is not disposed at a position corresponding to the high bending stiffness portion 22A. Namely, the heating element 72 does not have a function of heating the portion of the full length extending shape-memory pipe 42A constituting the high bending stiffness portion 22A. For this reason, the bending stiffness of the high bending stiffness portion 22A is determined by the hardness of the hard pipe 52A, and remains unchanged.

As described above, the heating element 72 is constituted of, for example, a coil heater, and is disposed adjacent to the shape-memory pipe 40A. The heating element 72 is disposed, for example, in direct contact with the shape-memory pipe 40A. A distance between the heating elements 72 along the longitudinal axis in FIG. 2, for example, corresponds to a distance between the low bending stiffness portions 24A.

In the variable stiffness device 10A, at least the portion of the first elongated member 20A is installed in the flexible member. The current supply unit 80 may be disposed outside the flexible member, or may be disposed inside the flexible member. The portion of the first elongated member 20A of the variable stiffness device 10A is disposed with a small clearance in a limited space of the flexible member so that at least one end of the first elongated member 20A is a free end. With such an arrangement, when the shape-memory pipe 40A undergoes phase transformation to contract, the shape-memory pipe 40A is prevented from being damaged due to the strong contraction force of the shape-memory pipe 40A, and stable use can be expected.

Herein, the limited space means a space that can just contain the first elongated member 20A of the variable stiffness device 10A. Therefore, deformation, even if it is slight, of one of the first elongated member 20A and the flexible member can contact the other to give an external force.

For example, it may be that the flexible member is a tube having an inner diameter slightly larger than the outer diameter of the first elongated member 20A, and at least the portion of the first elongated member 20A of the variable stiffness device 10A is disposed inside the tube. Not limited to this, the flexible member only needs to have a space slightly larger than the first elongated member 20A.

A single variable stiffness device 10A may be installed in the flexible member, or variable stiffness devices 10A may be installed in the flexible member. For example, the plurality of variable stiffness devices 10A may be installed in the flexible member with the portions of the first elongated members 20A being aligned along the longitudinal axis.

When the shape-memory pipe 40A is in the first phase, the variable stiffness device 10A provides relatively low stiffness to the flexible member, and easily deforms according to an external force acting on the flexible member, i.e., a force that can cause the shape-memory pipe 40A to deform.

When the shape-memory pipe 40A is in the second phase, the variable stiffness device 10A provides relatively high stiffness to the flexible member, and tends to return to a memory shape against an external force acting on the flexible member, i.e., a force that can cause the shape-memory pipe 40A to deform.

The current supply unit 80 supplies a current to the heater 70, whereby the phase of the shape-memory pipe 40A is switched from the first phase to the second phase. After that, the current supply unit 80 stops the supply of current to the heater 70, whereby the phase of the shape-memory pipe 40A is switched from the second phase to the first phase. Thereby, the stiffness of the portion of the flexible member in which the portion of the first elongated member 20A of the variable stiffness device 10A is installed is switched.

In addition to the switching of the stiffness, in a situation where an external force acts on the flexible member, the variable stiffness device 10A also functions as a bidirectional actuator configured to switch the shape of the flexible member. Also, in a situation where no external force other than gravity acts on the flexible member and the flexible member is deformed in the first phase before the phase of the shape-memory pipe 40A is switched to the second phase, the variable stiffness device 10A also functions as a unidirectional actuator configured to restore the shape of the flexible member to an original shape.

Working Effect

Next, a working effect of varying the stiffness of the variable stiffness device 10A according to the present embodiment will be described with reference to FIGS. 1A and 1B.

In the variable stiffness device 10A, the portion of the hard pipe 52A, i.e., the high bending stiffness portion 22A, always has high stiffness, so as to be relatively difficult to bend. The portion between two adjacent hard pipes 52A, i.e., the low bending stiffness portion 24A, is easier to bend than the high bending stiffness portion 22A, but the bendability varies depending on the state of the phase of the shape-memory pipe 40A of that portion.

In the variable stiffness device 10A in the soft state shown in FIG. 1A, no current is supplied to the heater 70. Thus, the shape-memory pipe 40A is in the first phase, e.g., the martensitic phase, so as to be in the low stiffness state. The hard pipe 52A has higher stiffness than that of the shape-memory pipe 40A. Accordingly, in the variable stiffness device 10A in the soft state shown in FIG. 1A, the portion of the hard pipe 52A, i.e., the high bending stiffness portion 22A, is relatively difficult to bend, and the portion between the adjacent two hard pipes 52A, i.e., the low bending stiffness portion 24A, is relatively easy to bend.

In the variable stiffness device 10A in the hard state shown in FIG. 1B, a current is supplied to the heater 70, so that the portion of the heater 70 between the two hard pipes 52A on the left side of FIG. 1B generates heat. The heat is efficiently transferred to the portion of the shape-memory pipe 40A. As a result, a portion 102 of the full length extending shape-memory pipe 42A expanding beyond the part between the two hard pipes 52A on the left side of FIG. 1B is heated, so that the temperature thereof rises. In FIG. 1B, the temperature rising portion 102 of the full length extending shape-memory pipe 42A is shown shaded with dots. The temperature rising portion 102 of the full length extending shape-memory pipe 42A undergoes phase transformation, so as to transition in phase from the first phase, e.g., the martensitic phase, to the second phase, e.g., the austenitic phase. As a result, the temperature rising portion 102 of the full length extending shape-memory pipe 42A has high stiffness. Thus, a portion 104 of the first elongated member 20A including the two hard pipes 52A on the left side of FIG. 1B and the temperature rising portion 102 of the full length extending shape-memory pipe 42A has high stiffness as a whole, so as to be more difficult to bend than when in the soft state shown in FIG. 1A.

In this way, it is possible to selectively increase the stiffness of the specific low bending stiffness portion 24A as compared with the soft state shown in FIG. 1A by supplying a current to the heater 70.

Immediately after the supply of current to the heater 70 is stopped, the temperature rising portion 102 of the full length extending shape-memory pipe 42A is still in the state of having heat upon heating, in the second phase, e.g., the austenitic phase, so as to be in the high stiffness state. Thereafter, the temperature of the temperature rising portion 102 of the full length extending shape-memory pipe 42A decreases by natural heat dissipation. As the temperature decreases, the temperature rising portion 102 of the full length extending shape-memory pipe 42A transitions in phase from the second phase, e.g., the austenitic phase, to the first phase, e.g., the martensitic phase. As a result, the variable stiffness device 10A transitions to the soft state shown in FIG. 1A again, so that the low bending stiffness portion 24A between the two hard pipes 52A on the left side of FIG. 1A has low stiffness, and is easier to bend than when in the hard state shown in FIG. 1B.

In this way, the variable stiffness device 10A can provide partially different stiffness to the flexible member in which it is installed. Specifically, the variable stiffness device 10A can provide different stiffness to the portion of the flexible member where the low bending stiffness portion 24A of the first elongated member 20A is disposed.

The hard pipe 52A preferably has high thermal conductivity on order to promote natural heat dissipation. Natural heat dissipation may be promoted by installing a graphite sheet with good thermal conductivity on the hard pipe 52A to promote heat conduction to the outside. As a result, by the temperature decrease, a time required for the temperature rising portion 102 of the full length extending shape-memory pipe 42A to return from the high stiffness state to the low stiffness state is shortened.

Advantageous Effect

In the variable stiffness device 10A of the present embodiment, by selectively changing the presence or absence of the current supply from the heater 70 to a specific heating element 72, the stiffness of the low bending stiffness portion 24A corresponding to that heating element 72 can be changed. This allows providing partially different stiffness to the flexible member in which the variable stiffness device 10A is installed.

The heater 70 extends through the inner space of the full length extending shape-memory pipe 42A. Thus, the heating element 72 of the heater 70 is disposed adjacent to the full length extending shape-memory pipe 42A. For example, the heating element 72 is disposed in direct contact with the full length extending shape-memory pipe 42A. Accordingly, the heat generated by the heating element 72 is efficiently transferred to the full length extending shape-memory pipe 42A. Thereby, rapid phase transformation of the full length extending shape-memory pipe 42A from the first phase to the second phase is obtained. Thus, in the transition from the soft state to the hard state, the variable stiffness device 10A has high responsiveness.

Second Embodiment

Configuration

Figure 3B:
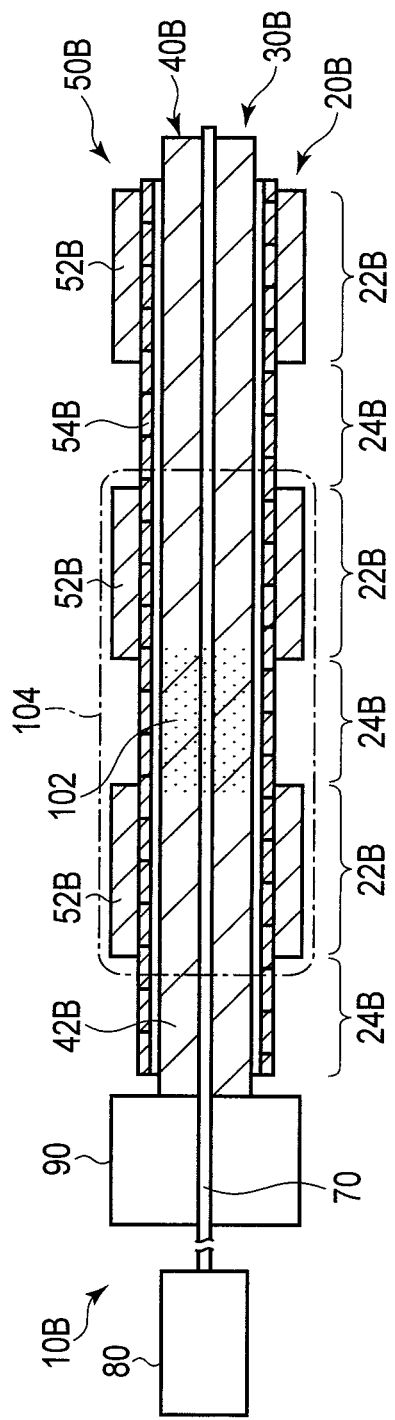
FIG. 3B shows the variable stiffness device according to the second embodiment.
Figure 3C:
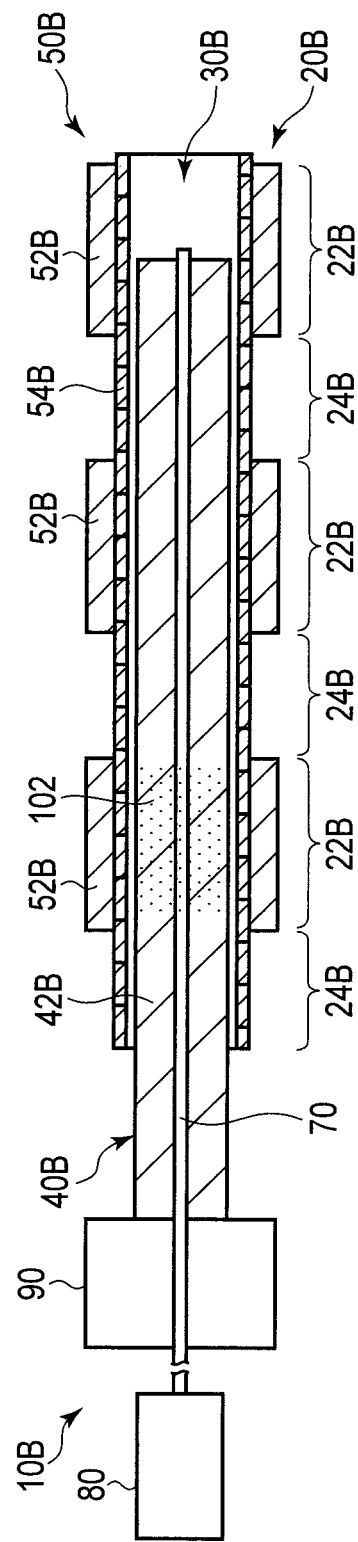
FIG. 3C shows the variable stiffness device according to the second embodiment.

FIGS. 3A, 3B, and 3C show a variable stiffness device 10B according to a second embodiment. The variable stiffness device 10B is a device that is to be installed in a flexible member, which is an object to be installed, and is configured to provide partially different stiffness to the flexible member. FIGS. 3A and 3C depict the variable stiffness device 10B in a soft state that provides partially relatively low stiffness to the flexible member, and FIG. 3B depicts the variable stiffness device 10B in a hard state that provides relatively high stiffness to the flexible member.

As shown in FIGS. 3A, 3B, and 3C, the variable stiffness device 10B includes a first elongated member 20B and a second elongated member 30B. The first elongated member 20B extends along the longitudinal axis. Similarly to the first elongated member 20B, the second elongated member 30B extends along the longitudinal axis, and is disposed along and adjacent to the first elongated member 20B. The first elongated member 20B and the second elongated member 30B are disposed so as to be relatively movable along the longitudinal axis.

The variable stiffness device 10B also includes a moving mechanism 90 configured to move the second elongated member 30B along the longitudinal axis relative to the first elongated member 20B.

The first elongated member 20B includes high bending stiffness portions 22B and low bending stiffness portions 24B. The high bending stiffness portions 22B and the low bending stiffness portions 24B are alternately arranged along the longitudinal axis of the first elongated member 20B. The high bending stiffness portion 22B has higher bending stiffness than that of the low bending stiffness portion 24B. For this reason, the first elongated member 20B is relatively easy to bend at the portion of the low bending stiffness portion 24B, and relatively difficult to bend at the portion of the high bending stiffness portion 22B.

The first elongated member 20B does not necessarily have to include high bending stiffness portions 22B and low bending stiffness portions 24B. The first elongated member 20B only needs to include at least one high bending stiffness portion 22B and at least one low bending stiffness portion 24B.

The first elongated member 20B is constituted of a pipe 50B, and includes a single soft pipe 54B continuously extending over substantially the entire length of the first elongated member 20B and hard pipes 52B spaced apart from one another along the soft pipe 54B and disposed around the soft pipe 54B. A distance between the hard pipes 52B may or may not be constant. In other words, the pipe 50B is constituted of the single soft pipe 54B and the hard pipes 52B.

The meaning that the soft pipe 54B extends over substantially the entire length of the first elongated member 20B is the same as the meaning described in association with the full length extending shape-memory pipe 42A in the first embodiment.

The hard pipe 52B has higher stiffness than that of the soft pipe 54B. The hard pipe 52B constitutes a part of the high bending stiffness portion 22B, and a part of the soft pipe 54B constitutes the low bending stiffness portion 24B. Specifically, the hard pipe 52B constitutes the high bending stiffness portion 22B together with a covered portion of the soft pipe 54B that is covered by the hard pipe 52B. An exposed portion of the soft pipe 54B that is not covered by the hard pipe 52B constitutes the low bending stiffness portion 24B.

The soft pipe 54B is configured of, for example, a coil pipe. The coil pipe may be a tightly-wound coil or a loosely-wound coil. The soft pipe 54B is preferably made of a material having good thermal conductivity. The soft pipe 54B may be configured by shape memory.

Each hard pipe 52B is constituted of, for example, a pipe of SUS (stainless steel). Each hard pipe 52B is preferably made of a material having good thermal conductivity. Each hard pipe 52B is fixed to the soft pipe 54B. Fixing of each hard pipe 52B to the soft pipe 54B may be performed, for example, by brazing or caulking.

The second elongated member 30B includes a shape-memory pipe 40B extending along the longitudinal axis. The shape-memory pipe 40B is disposed in an inner space of the pipe 50B constituting the first elongated member 20B. That is, the shape-memory pipe 40B is disposed in the inner space of the soft pipe 54B. The shape-memory pipe 40B is constituted of a full length extending shape-memory pipe 42B extending continuously over substantially the entire length of the second elongated member 30B.

The second elongated member 30B also includes the heater 70 extending through an inner space of the full length extending shape-memory pipe 42B. The heater 70 is fixed to the full length extending shape-memory pipe 42B so that a relative positional relationship with the full length extending shape-memory pipe 42B will not change.

The heater 70 has a function of causing the full length extending shape-memory pipe 42B to transition in phase between the first phase and the second phase by receiving a supply of current to generate heat. The heater 70 is electrically connected to the current supply unit 80 configured to supply a current to the heater 70.

Details of the heater 70 and the current supply unit 80 are as described in the first embodiment. Various characteristics of the shape-memory pipe 40B, i.e., the full length extending shape-memory pipe 42B, are the same as those of the shape-memory pipe 40A of the first embodiment, i.e., the full length extending shape-memory pipe 42A.

The shape-memory pipe 40B and the heater 70 are connected to the moving mechanism 90 configured to move the second elongated member 30B along the longitudinal axis relative to the first elongated member 20B. Namely, the shape-memory pipe 40B and the heater 70 included in the second elongated member 30B are held movably in the longitudinal axis by the moving mechanism 90. The moving mechanism 90 may be constituted of, for example, but is not limited to, a wire with an end connected to the second elongated member 30B and a motor configured to rotate a take-up pulley to which the other end of the wire is fixed.

For example, the moving mechanism 90 moves the second elongated member 30B along the longitudinal axis relative to the first elongated member 20B so that the portion of the full length extending shape-memory pipe 42B that will be heated by the heater 70 is disposed in an inner space of the low bending stiffness portion 24B, and so that the portion of the full length extending shape-memory pipe 42B that has been heated by the heater 70 is disposed in an inner space of the high bending stiffness portion 22B.

As described with reference to FIG. 2 in association with the first embodiment, the heater 70 includes heating elements 72 spaced apart from one another along the longitudinal axis. Although not shown in FIGS. 3A, 3B, and 3C, in the state shown in FIGS. 3A and 3B, the heating elements 72 are disposed so as to heat at least the portions of the full length extending shape-memory pipe 42B located at the low bending stiffness portions 24B. In the state shown in FIG. 3C, the heating elements 72 are disposed so as to be at the high bending stiffness portions 22B.

The length of each heating element 72 is longer than the length of the low bending stiffness portion 24B, where that heating element 72 can be disposed. The length of each heating element 72 is also, for example, shorter than the length of the high bending stiffness portion 22B, where the heating element 72 can be disposed. Preferably, the length of the portion of the full length extending shape-memory pipe 42B that is heated by the heating element 72 is longer than the length of the high bending stiffness portion 22B. Herein, the length means a dimension along the longitudinal axis.

The variable stiffness device 10B is installed in a flexible member, similarly to the first embodiment. The first elongated member 20B is arranged so as not to move relative to the flexible member. The first elongated member 20B is disposed with a small clearance in a limited space of the flexible member so that at least one end of the first elongated member 20B is a free end. On the other hand, the second elongated member 30B is disposed movably relative to the first elongated member 20B.

Similarly to the first embodiment, a single variable stiffness device 10B may be installed in the flexible member, or variable stiffness devices 10B may be installed in the flexible member.

Working Effect

Next, a working effect of varying the stiffness of the variable stiffness device 10B of the present embodiment will be described with reference to FIGS. 3A, 3B, and 3C. In the variable stiffness device 10B depicted in FIGS. 3A and 3B, the portion of the full length extending shape-memory pipe 42B that will be heated by the heating element 72 of the heater 70 is disposed in the inner space of the low bending stiffness portion 24B. In the variable stiffness device 10B depicted in FIG. 3C, the portion of the full length extending shape-memory pipe 42B that has been heated by the heating element 72 of the heater 70 is disposed in the inner space of the high bending stiffness portion 22B.

In the variable stiffness device 10B, the portion of the hard pipe 52B, i.e., the high bending stiffness portion 22B, always has high stiffness, so as to be relatively difficult to bend. The portion between two adjacent hard pipes 52B, i.e., the low bending stiffness portion 24B, is easier to bend than the high bending stiffness portion 22B.

In the variable stiffness device 10B in the soft state shown in FIG. 3A, no current is supplied to the heater 70. Thus, the full length extending shape-memory pipe 42B is in the first phase, e.g., the martensitic phase, so as to be in the low stiffness state. In the variable stiffness device 10B in the soft state shown in FIG. 3A, the portion of the hard pipe 52B, i.e., the high bending stiffness portion 22B, is relatively difficult to bend, and the portion between the two adjacent hard pipes 52B, i.e., the low bending stiffness portion 24B, is relatively easy to bend.

In the variable stiffness device 10B in the hard state shown in FIG. 3B, a current is supplied to the heater 70, so that the heating element 72 between the two hard pipes 52B on the left side of FIG. 3B generates heat. The heat is efficiently transferred to the full length extending shape-memory pipe 42B. As a result, the portion 102 of the full length extending shape-memory pipe 42B expanding beyond the part between the two hard pipes 52B on the left side of FIG. 3B is heated, so that the temperature thereof rises. In FIG. 3B, the temperature rising portion 102 of the full length extending shape-memory pipe 42B is shown shaded with dots. The temperature rising portion 102 of the full length extending shape-memory pipe 42B undergoes phase transformation, so as to transition in phase from the first phase, e.g., the martensitic phase, to the second phase, e.g., the austenitic phase. As a result, the temperature rising portion 102 of the full length extending shape-memory pipe 42B provides high stiffness to the portion of the soft pipe 54B between the two hard pipes 52B on the left side of FIG. 3B. In other words, the temperature rising portion 102 of the full length extending shape-memory pipe 42B causes the portion of the soft pipe 54B around the portion 102 to be difficult to bend. Thereby, the portion 104 of the first elongated member 20B including the portion of the soft pipe 54B between the two hard pipes 52B on the left side of FIG. 3B and the two hard pipes 52B is more difficult to bend than when in the soft state shown in FIG. 3A.

In this way, it is possible to selectively cause a specific low bending stiffness portion 24B to be difficult to bend as compared with the soft state shown in FIG. 3A by supplying a current to the heater 70.

Immediately after the supply of current to the heater 70 is stopped, the temperature rising portion 102 of the full length extending shape-memory pipe 42B is still in the state of having heat upon heating, in the second phase, e.g., the austenitic phase, so as to be in the high stiffness state. Therefore, simply by stopping the supply of current to the heater 70, the variable stiffness device 10B in the hard state will not enter the soft state immediately.

In the present embodiment, when returning the variable stiffness device 10B in the hard state to the soft state, although temperature decrease of the full length extending shape-memory pipe 42B by natural heat dissipation may be waited for, but preferably, instead, as shown in FIG. 3C, the second elongated member 30B is moved by the moving mechanism 90 along the longitudinal axis relative to the first elongated member 20B so that the temperature rising portion 102 of the full length extending shape-memory pipe 42B that has been heated by the heater 70 is disposed in the inner space of the high bending stiffness portion 22B. As a result, in the low bending stiffness portion 24B where the temperature rising portion 102 of the full length extending shape-memory pipe 42B has been disposed, the portion of the full length extending shape-memory pipe 42B that has not been heated, i.e., the portion of the full length extending shape-memory pipe 42B in the low stiffness state, is disposed. As a result, that low bending stiffness portion 24B is easier to bend than when in the hard state shown in FIG. 3B.

In the present embodiment, since the temperature rising portion 102 of the full length extending shape-memory pipe 42B is moved into the inner space of the high bending stiffness portion 22B when returning the variable stiffness device 10B in the hard state to the soft state, the variable stiffness device 10B can be returned to the soft state in a time shorter than the time required for waiting for the temperature decrease of the full length extending shape-memory pipe 42B by natural heat dissipation.

In this way, the variable stiffness device 10B can provide partially different stiffness to the flexible member in which it is installed. Specifically, the variable stiffness device 10B can provide different stiffness to the portion of the flexible member where the low bending stiffness portion 24B of the first elongated member 20B is disposed.

The hard pipe 52B preferably has high thermal conductivity in order to promote natural heat dissipation of the temperature rising portion 102 of the full length extending shape-memory pipe 42B. Natural heat dissipation may be promoted by installing a graphite sheet with good thermal conductivity on the hard pipe 52B to promote heat conduction to the outside. As a result, by the temperature decrease, a time required for the temperature rising portion 102 of the full length extending shape-memory pipe 42B to return from the high stiffness state to the low stiffness state is shortened.

Advantageous Effect

In the variable stiffness device 10B of the present embodiment, by selectively changing the presence or absence of a current supply to a specific heating element 72 of the heater 70, the stiffness of the low bending stiffness portion 24B corresponding to that heating element 72 can be changed. This allows providing partially different stiffness to the flexible member in which the variable stiffness device 10B is installed.

The heater 70 extends through the inner space of the full length extending shape-memory pipe 42B. Thus, the heating element 72 of the heater 70 is disposed adjacent to the full length extending shape-memory pipe 42B. For example, the heating element 72 is disposed in direct contact with the full length extending shape-memory pipe 42B. Accordingly, the heat generated by the heating element 72 is efficiently transferred to the full length extending shape-memory pipe 42B. Thereby, rapid phase transformation of the full length extending shape-memory pipe 42B from the first phase to the second phase is obtained. Thus, in the transition from the soft state to the hard state, the variable stiffness device 10B has high responsiveness.

In addition, since the temperature rising portion 102 of the full length extending shape-memory pipe 42B is moved into the inner space of the high bending stiffness portion 22B when returning the variable stiffness device 10B in the hard state to the soft state, the variable stiffness device 10B can be returned to the soft state in a time shorter than the time required for waiting for the temperature decrease of the full length extending shape-memory pipe 42B by natural heat dissipation. Thus, in the transition from the hard state to the soft state, the variable stiffness device 10B has high responsiveness.

In the present embodiment, the hard pipe 52B of the first elongated member 20B is separated from the full length extending shape-memory pipe 42B. In contrast, in the first embodiment, the hard pipe 52A of the first elongated member 20A is in contact with the full length extending shape-memory pipe 42A. In addition, the hard pipe 52B of the first elongated member 20B of the present embodiment is located farther from the heater 70 than the hard pipe 52A of the first elongated member 20A of the first embodiment. Thus, the hard pipe 52B of the present embodiment is less likely to be heated by the heater 70 than the hard pipe 52A of the first embodiment. Thereby, the heat dissipation efficiency of the full length extending shape-memory pipe 42B of the present embodiment is superior to that of the full length extending shape-memory pipe 42A of the first embodiment.

Modification of Second Embodiment

FIG. 4 shows a variable stiffness device 10C according to a modification of the second embodiment. The variable stiffness device 10C has a configuration in which the first elongated member 20B in the variable stiffness device 10B is replaced with a first elongated member 20C.

As shown in FIG. 4, the variable stiffness device 10C includes the first elongated member 20C and the second elongated member 30B. The first elongated member 20C extends along the longitudinal axis. Similarly to the first elongated member 20C, the second elongated member 30B extends along the longitudinal axis, and is disposed along and adjacent to the first elongated member 20C. The first elongated member 20C and the second elongated member 30B are disposed so as to be relatively movable along the longitudinal axis.

Details of the second elongated member 30B (i.e., the shape-memory pipe 40B and the heater 70), the current supply unit 80, and the moving mechanism 90, are as described above.

The first elongated member 20C includes high bending stiffness portions 22C and low bending stiffness portions 24C. The high bending stiffness portions 22C and the low bending stiffness portions 24C are alternately arranged along the longitudinal axis of the first elongated member 20C. The high bending stiffness portion 22C has higher bending stiffness than that of the low bending stiffness portion 24C. For this reason, the first elongated member 20C is relatively easy to bend at the portion of the low bending stiffness portion 24C, and relatively difficult to bend at the portion of the high bending stiffness portion 22C.

The first elongated member 20C is constituted of a slitted hard pipe 50C. The slitted hard pipe 50C includes non-slit portions 52C and slit portions 54C alternately arranged along the longitudinal axis of the first elongated member 20C. The slit portion 54C is constituted of a portion where a slit is formed in a hard pipe that is a base material of the slitted hard pipe 50C. In addition, the non-slit portion 52C is constituted of a portion where a slit is not formed in the hard pipe as the base material of the slitted hard pipe 50C.

The non-slit portion 52C has higher stiffness than that of the slit portion 54C. The non-slit portion 52C constitutes the high bending stiffness portion 22C, and the slit portion 54C constitutes the low bending stiffness portion 24C.

The slitted hard pipe 50C may be made from, for example, a pipe of SUS (stainless steel). The slitted hard pipe 50C is preferably made of a material having good thermal conductivity.

The variable stiffness device 10C according to the present modification is the same as the variable stiffness device 10B, except for the first elongated member 20C. The first elongated member 20C is functionally the same as the first elongated member 20B. Therefore, the operation, etc. of the variable stiffness device 10C are the same as those of the variable stiffness device 10B according to the second embodiment.

Since the slitted hard pipe 50C is produced by processing a single hard pipe, the slitted hard pipe 50C has less influence of tolerance than the pipe 50B constituted of the soft pipe 54B and the hard pipes 52B. In addition, the slitted hard pipe 50C can be formed smaller than the pipe 50B. Thereby, the variable stiffness device 10C according to the present modification can be configured to be smaller than the variable stiffness device 10B according to the second embodiment.

Third Embodiment

Configuration

FIGS. 5A and 5B show a variable stiffness device 10D according to a third embodiment. The variable stiffness device 10D is a device that is to be installed in a flexible member, which is an object to be installed, and is configured to provide partially different stiffness to the flexible member. FIG. 5A depicts the variable stiffness device 10D in a soft state that provides partially relatively low stiffness to the flexible member, and FIG. 5B depicts the variable stiffness device 10D in a hard state that provides relatively high stiffness to the flexible member.

As shown in FIGS. 5A and 5B, the variable stiffness device 10D includes a first elongated member 20D and a second elongated member 30D. The first elongated member 20D extends along the longitudinal axis. Similarly to the first elongated member 20D, the second elongated member 30D extends along the longitudinal axis, and is disposed along and adjacent to the first elongated member 20D. The first elongated member 20D and the second elongated member 30D are fixed to each other so that their relative position will not change.

The first elongated member 20D includes high bending stiffness portions 22D and low bending stiffness portions 24D. The high bending stiffness portions 22D and the low bending stiffness portions 24D are alternately arranged along the longitudinal axis of the first elongated member 20D. The high bending stiffness portion 22D has higher bending stiffness than that of the low bending stiffness portion 24D. For this reason, the first elongated member 20D is relatively easy to bend at the portion of the low bending stiffness portion 24D, and relatively difficult to bend at the portion of the high bending stiffness portion 22D.

The first elongated member 20D does not necessarily have to include high bending stiffness portions 22D and low bending stiffness portions 24D. The first elongated member 20D only needs to include at least one high bending stiffness portion 22D and at least one low bending stiffness portion 24D. For example, the first elongated member 20D may be a configuration including two high bending stiffness portions 22D and one low bending stiffness portion 24D.

The first elongated member 20D is constituted of a pipe 50D, and includes a shape-memory pipe 40D extending along the longitudinal axis. The shape-memory pipe 40D is constituted of a partially extending shape-memory pipe 44D partially extending along the longitudinal axis of the first elongated member 20D. For example, the shape-memory pipe 40D is constituted of partially extending shape-memory pipes 44D spaced apart from one another along the longitudinal axis of the first elongated member 20D. The first elongated member 20D also includes a hard pipe 52D partially extending along the longitudinal axis. For example, the first elongated member 20D includes hard pipes 52D spaced apart from one another along the longitudinal axis. Each partially extending shape-memory pipe 44D connects two adjacent hard pipes 52D spaced apart from each other along the longitudinal axis. A distance between the hard pipes 52D may or may not be constant. In other words, the pipe 50D is constituted of partially extending shape-memory pipes 44D and hard pipes 52D.

The hard pipe 52D has higher stiffness than that of the partially extending shape-memory pipe 44D. The hard pipe 52D constitutes a part of the high bending stiffness portion 22D, and a part of the partially extending shape-memory pipe 44D constitutes the low bending stiffness portion 24D. Specifically, the hard pipe 52D constitutes the high bending stiffness portion 22D together with a covered portion of the partially extending shape-memory pipe 44D that is covered by the hard pipe 52D. In addition, an exposed portion of the partially extending shape-memory pipe 44D that is not covered by the hard pipe 52D constitutes the low bending stiffness portion 24D. The stiffness of the low bending stiffness portion 24D varies depending on the state of the phase of the partially extending shape-memory pipe 44D of that portion. That is, the low bending stiffness portion 24D can be considered to be a variable bending stiffness portion. The low bending stiffness portion 24D has higher stiffness when the partially extending shape-memory pipe 44D of that portion is in the high stiffness state than when in the low stiffness state.

Each hard pipe 52D is constituted of, for example, a pipe of SUS (stainless steel). Each hard pipe 52D is preferably made of a material having good thermal conductivity. Each hard pipe 52D is fixed to the partially extending shape-memory pipe 44D. Fixing of each hard pipe 52D to the partially extending shape-memory pipe 44D may be performed, for example, by brazing or caulking.

The second elongated member 30D includes the heater 70 extending through the inner space of the partially extending shape-memory pipe 44D. The heater 70 is fixed to the partially extending shape-memory pipe 44D so that a relative positional relationship with the partially extending shape-memory pipe 44D will not change.

The heater 70 has a function of causing the partially extending shape-memory pipe 44D to transition in phase between the first phase and the second phase by receiving a supply of current to generate heat. The heater 70 is electrically connected to a current supply unit 80 configured to supply a current to the heater 70.

Details of the heater 70 and the current supply unit 80 are as described in the first embodiment. Various characteristics of the shape-memory pipe 40D, i.e., the partially extending shape-memory pipe 44D, are the same as those of the shape-memory pipe 40A of the first embodiment, i.e., the full length extending shape-memory pipe 42A.

As described with reference to FIG. 2 in association with the first embodiment, the heater 70 includes heating elements 72 spaced apart from one another along the longitudinal axis. Although not shown in FIGS. 5A and 5B, the heating elements 72 are disposed between adjacent two of the hard pipes 52D spaced apart from one another along the longitudinal axis. That is, the heating element 72 has a function of heating the portion of the partially extending shape-memory pipe 44D between adjacent two of the high bending stiffness portions 22D. In other words, the heating element 72 is disposed at a position corresponding to the low bending stiffness portion 24D, and has a function of heating the portion of the partially extending shape-memory pipe 44D located in the low bending stiffness portion 24D.

The heating element 72 is constituted of, for example, a coil heater, and is disposed adjacent to the partially extending shape-memory pipe 44D. The heating element 72 is disposed, for example, in direct contact with the partially extending shape-memory pipe 44D.

The heater 70 does not necessarily have to have the function of heating all the partially extending shape-memory pipes 44D. That is, the heating elements 72 do not have to be disposed in all the low bending stiffness portions 24D, and may be disposed only in low bending stiffness portions 24D that is needed to be varied in bending stiffness The variable stiffness device 10D is installed in a flexible member, similarly to the first embodiment. The first elongated member 20D is disposed so as not to move relative to the flexible member. The first elongated member 20D is disposed with a small clearance in a limited space of the flexible member so that at least one end of the first elongated member 20D is a free end.

Similarly to the first embodiment, a single variable stiffness device 10D may be installed in the flexible member, or variable stiffness devices 10D may be installed.

Working Effect

Next, a working effect of varying the stiffness of the variable stiffness device 10D of the present embodiment will be described with reference to FIGS. 5A and 5B.

In the variable stiffness device 10D, the portion of the hard pipe 52D, i.e., the high bending stiffness portion 22D, always has high stiffness, so as to be relatively difficult to bend. The portion between two adjacent hard pipes 52D, i.e., the low bending stiffness portion 24D, is easier to bend than the high bending stiffness portion 22D, but the bendability varies depending on the state of the phase of the partially extending shape-memory pipe 44D of that portion.

In the variable stiffness device 10D in the soft state shown in FIG. 5A, no current is supplied to the heater 70. Thus, the partially extending shape-memory pipe 44D is in the first phase, e.g., the martensitic phase, so as to be in the low stiffness state. The hard pipe 52D has higher stiffness than that of the partially extending shape-memory pipe 44D. Accordingly, in the variable stiffness device 10D in the soft state shown in FIG. 5A, the portion of the hard pipe 52D, i.e., the high bending stiffness portion 22D, is relatively difficult to bend, and the portion between two adjacent hard pipes 52D, i.e., the low bending stiffness portion 24D, is relatively easy to bend.

In the variable stiffness device 10D in the hard state shown in FIG. 5B, a current is supplied to the heater 70, so that the portion of the heater 70 at the low bending stiffness portion 24D at the center of FIG. 5B generates heat. The heat is efficiently transferred to the low bending stiffness portion 24D. As a result, the partially extending shape-memory pipe 44D at the low bending stiffness portion 24D at the center of FIG. 5B is heated, so that the temperature thereof rises. In FIG. 5B, the heated partially extending shape-memory pipe 44D is shown shaded with dots. The heated partially extending shape-memory pipe 44D undergoes phase transformation, so as to transition in phase from the first phase, e.g., the martensitic phase, to the second phase, e.g., the austenitic phase. As a result, the low bending stiffness portion 24D at the center of FIG. 5B has high stiffness. Thus, a portion 104 of the first elongated member 20D including that low bending stiffness portion 24D and the two hard pipes 52D connected thereto has high stiffness as a whole, so as to be more difficult to bend than when in the soft state shown in FIG. 5A.

In this way, it is possible to selectively increase the stiffness of a specific low bending stiffness portion 24D as compared with the soft state shown in FIG. 5A by supplying a current to the heater 70.

Immediately after the supply of current to the heater 70 is stopped, the heated partially extending shape-memory pipe 44D is still in the state of having heat upon heating, in the second phase, e.g., the austenitic phase, so as to be in the high stiffness state. Thereafter, the temperature of the heated partially extending shape-memory pipe 44D decreases by natural heat dissipation. As the temperature decreases, the heated partially extending shape-memory pipe 44D transitions in phase from the second phase, e.g., the austenitic phase, to the first phase, e.g., the martensitic phase. As a result, the variable stiffness device 10D transitions again to the soft state shown in FIG. 5A, so that the low bending stiffness portion 24D at the center of FIG. 5A has low stiffness, and is easier to bend than when in the hard state shown in FIG. 5B.

In this way, the variable stiffness device 10D can provide partially different stiffness to a flexible member in which the variable stiffness device 10D is installed. Specifically, the variable stiffness device 10D can provide different stiffness to the portion of the flexible member where the low bending stiffness portion 24D of the first elongated member 20D is disposed.

The hard pipe 52D preferably has high thermal conductivity to promote natural heat dissipation. In addition, natural heat dissipation may be promoted by installing a graphite sheet with good thermal conductivity on the hard pipe 52D to promote heat conduction to the outside. As a result, by the temperature decrease, a time required for the heated partially extending shape-memory pipe 44D to return from the high stiffness state to the low stiffness state is shortened.

Advantageous Effect

In the variable stiffness device 10D of the present embodiment, by selectively changing the presence or absence of the current supply to a specific heating element 72 of the heater 70, the stiffness of the low bending stiffness portion 24D corresponding to that heating element 72 can be changed. This allows providing partially different stiffness to the flexible member in which the variable stiffness device 10D is installed.

The heater 70 extends through an inner space of the partially extending shape-memory pipe 44D. Thus, the heating element 72 of the heater 70 is disposed adjacent to the partially extending shape-memory pipe 44D. For example, the heating element 72 is disposed in direct contact with the partially extending shape-memory pipe 44D. Accordingly, the heat generated by the heating element 72 is efficiently transferred to the partially extending shape-memory pipe 44D. Thereby, rapid phase transformation of the partially extending shape-memory pipe 44D from the first phase to the second phase is obtained. Thus, the variable stiffness device 10D has high responsiveness.

The partially extending shape-memory pipes 44D are spaced apart from one another along the longitudinal direction. Thus, in the present embodiment, the volume of the partially extending shape-memory pipe 44D to be heated in order to harden the low bending stiffness portion 24D is smaller than the volume of the full length extending shape-memory pipe 42A to be heated to harden the low bending stiffness portion 24A in the first embodiment. Accordingly, in the transition from the soft state to the hard state, the variable stiffness device 10D of the present embodiment has higher responsiveness than the variable stiffness device 10A of the first embodiment.

Since the partially extending shape-memory pipes 44D are spaced apart from one another along the longitudinal direction, a partially extending shape-memory pipe 44D located next to the partially extending shape-memory pipe 44D to be heated is less likely to be undesirably heated.

Furthermore, the partially extending shape-memory pipe 44D of the present embodiment is shorter in length than the full length extending shape-memory pipe 42A of the first embodiment, so as to have excellent processability.

Fourth Embodiment

Configuration

Figure 6A:
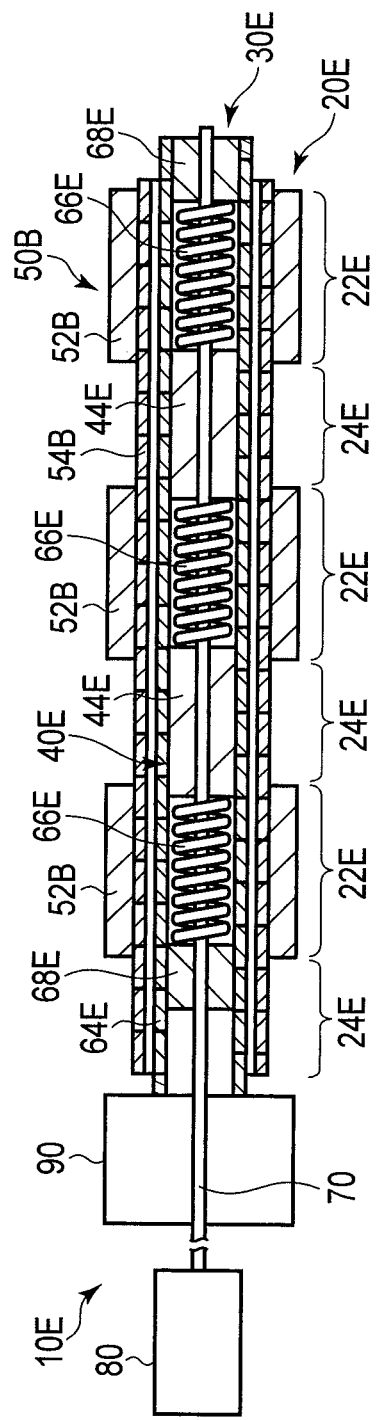
FIG. 6A shows a variable stiffness device according to a fourth embodiment.
Figure 6B:
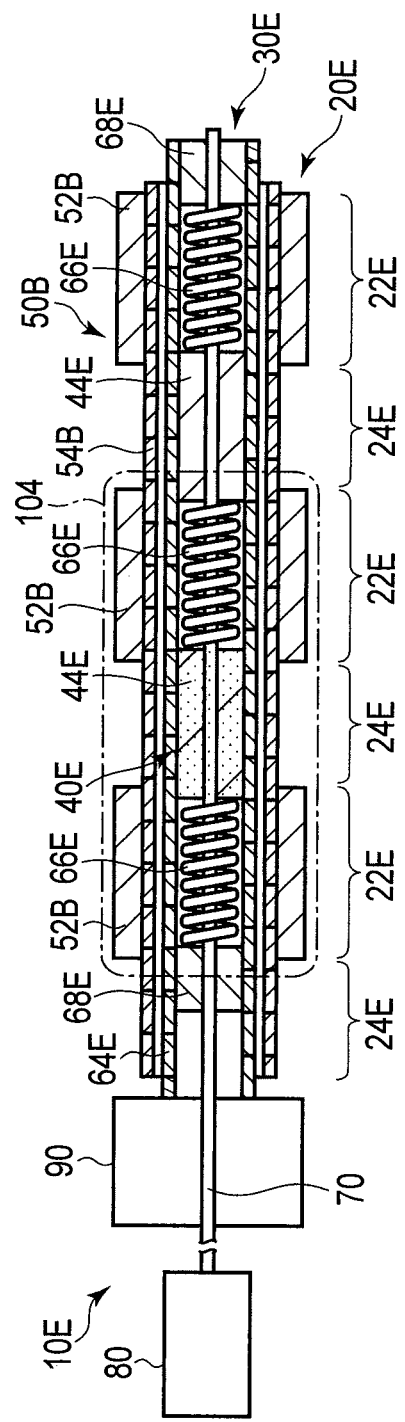
FIG. 6B shows the variable stiffness device according to the fourth embodiment.
Figure 6C:
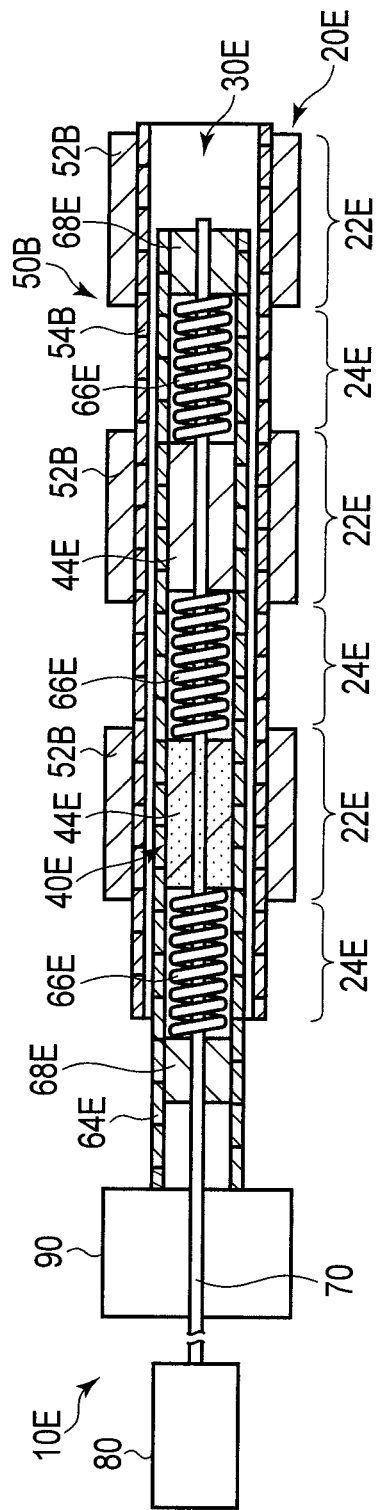
FIG. 6C shows the variable stiffness device according to the fourth embodiment.

FIGS. 6A, 6B, and 6C show a variable stiffness device 10E according to a fourth embodiment. The variable stiffness device 10E is a device that is to be installed in a flexible member, which is an object to be installed, and is configured to provide partially different stiffness to the flexible member. FIGS. 6A and 6C depict the variable stiffness device 10E in a soft state that provides partially relatively low stiffness to the flexible member, and FIG. 6B depicts the variable stiffness device 10E in a hard state that provides relatively high stiffness to the flexible member.

As shown in FIGS. 6A, 6B, and 6C, the variable stiffness device 10E includes a first elongated member 20E and a second elongated member 30E. The first elongated member 20E extends along the longitudinal axis. Similarly to the first elongated member 20E, the second elongated member 30E extends along the longitudinal axis, and is disposed along and adjacent to the first elongated member 20E. The first elongated member 20E and the second elongated member 30E are disposed so to be relatively movable along the longitudinal axis.

The variable stiffness device 10E also includes the moving mechanism 90 configured to move the second elongated member 30E along the longitudinal axis relative to the first elongated member 20E.

The first elongated member 20E includes high bending stiffness portions 22E and low bending stiffness portions 24E. The high bending stiffness portions 22E and the low bending stiffness portions 24E are alternately arranged along the longitudinal axis of the first elongated member 20E. The high bending stiffness portion 22E has higher bending stiffness than that of the low bending stiffness portion 24E. For this reason, the first elongated member 20E is relatively easy to bend at the portion of the low bending stiffness portion 24E, and is relatively difficult to bend at the portion of the high bending stiffness portion 22E.

The first elongated member 20E does not necessarily have to include high bending stiffness portions 22E and low bending stiffness portions 24E. The first elongated member 20E only needs to include at least one high bending stiffness portion 22E and at least one low bending stiffness portion 24E.

The first elongated member 20E is constituted of a pipe 50B, similarly to the first elongated member 20B in the second embodiment. That is, the configuration of the first elongated member 20E is the same as that of the first elongated member 20B in the second embodiment. Details of the first elongated member 20B or the pipe 50B are as described in the second embodiment.

Accordingly, the high bending stiffness portion 22E is constituted of the hard pipe 52B and a covered portion of the soft pipe 54B that is covered by the hard pipe 52B. In addition, the low bending stiffness portion 24E is constituted of an exposed portion of the soft pipe 54B that is not covered by the hard pipe 52B. The length of the high bending stiffness portion 22E is longer than that of the low bending stiffness portion 24E.

The second elongated member 30E includes a single soft pipe 64E continuously extending over substantially the entire length of the second elongated member 30E. The soft pipe 64E is inserted into the inner space of the pipe 50B constituting the first elongated member 20E.

The second elongated member 30E also includes a shape-memory pipe 40E disposed in an inner space of the soft pipe 64E. The shape-memory pipe 40E is constituted of a partially extending shape-memory pipe 44E partially extending along the longitudinal axis of the first elongated member 20E. For example, the shape-memory pipe 40E is constituted of partially extending shape-memory pipes 44E spaced apart from one another along the longitudinal axis of the first elongated member 20E.

The length of each partially extending shape-memory pipe 44E is longer than that of the low bending stiffness portion 24E where that partially extending shape-memory pipe 44E can be disposed. The length of each partially extending shape-memory pipe 44E is also preferably shorter than that of the high bending stiffness portion 22E where that partially extending shape-memory pipe 44E can be disposed.

Alternatively, the length of the portion of each partially extending shape-memory pipe 44E heated by the heater 70 is longer than that of the low bending stiffness portion 24E where that partially extending shape-memory pipe 44E can be disposed, and is preferably shorter than that of the high bending stiffness portion 22E where that partially extending shape-memory pipe 44E can be disposed.

The second elongated member 30E further includes springs 66E and fixing member 68Es disposed in the inner space of the soft pipe 64E, in addition to the partially extending shape-memory pipes 44E. Each partially extending shape-memory pipe 44E is disposed between two springs 66E. The fixing members 68E are disposed outside the springs 66E at both ends. The partially extending shape-memory pipes 44E, the springs 66E, and the fixing members 68E are disposed in contact with each other. The fixing members 68E are fixed to the soft pipe 64E. The springs 66E function to position the partially extending shape-memory pipes 44E with respect to the fixing members 68E.

In the configurations shown in FIGS. 6A, 6B, and 6C, the springs 66E at the both ends are fixed to the soft pipe 64E through the fixing members 68E, but alternatively, the fixing members 68E may be omitted, and outer ends of the springs 66E at the both ends may be directly fixed to the soft pipe 64E.

The second elongated member 30E also includes the heater 70 extending through an inner space of the partially extending shape-memory pipe 44E. The heater 70 has a function of causing the partially extending shape-memory pipe 44E to transition in phase between the first phase and the second phase by receiving a supply of current to generate heat. The heater 70 is electrically connected to a current supply unit 80 configured to supply a current to the heater 70.

Details of the heater 70 and the current supply unit 80 are as described in the first embodiment. Various characteristics of the shape-memory pipe 40E, i.e., the partially extending shape-memory pipe 44E, are the same as those of the shape-memory pipe 40A of the first embodiment, i.e., the full length extending shape-memory pipe 42A.

The soft pipe 64E and the heater 70 are connected to the moving mechanism 90 configured to move the second elongated member 30E along the longitudinal axis relative to the first elongated member 20E. Namely, the soft pipe 64E and the heater 70 included in the second elongated member 30E are held movably in the longitudinal axis by the moving mechanism 90. For example, the moving mechanism 90 moves the second elongated member 30E along the longitudinal axis relative to the first elongated member 20E so that the partially extending shape-memory pipe 44E is disposed in an inner space of the low bending stiffness portion 24E, and so that the partially extending shape-memory pipe 44E is disposed in an inner space of the high bending stiffness portion 22E.

As described with reference to FIG. 2 in association with the first embodiment, the heater 70 includes heating elements 72 spaced apart from one another along the longitudinal axis. Although not shown in FIGS. 6A, 6B, and 6C, the heating elements 72 are disposed in the inner space of the partially extending shape-memory pipe 44E. The heating elements 72 are preferably disposed near the center of the partially extending shape-memory pipes 44E along the longitudinal axis.

The variable stiffness device 10E is installed in a flexible member, similarly to the first embodiment. The first elongated member 20E is disposed so as not to move relative to the flexible member. The first elongated member 20E is disposed with a small clearance in a limited space of the flexible member so that at least one end of the first elongated member 20E is a free end. On the other hand, the second elongated member 30E is disposed movably relative to the first elongated member 20E.

Similarly to the first embodiment, a single variable stiffness device 10E may be installed in the flexible member, or variable stiffness devices 10E may be installed in the flexible member.

Working Effect

Next, a working effect of varying the stiffness of the variable stiffness device 10E according to the present embodiment will be described with reference to FIGS. 6A, 6B, and 6C. In the variable stiffness device 10E depicted in FIGS. 6A and 6B, the partially extending shape-memory pipe 44E is disposed in the inner space of the low bending stiffness portion 24E. In addition, in the variable stiffness device 10E depicted in FIG. 6C, the partially extending shape-memory pipe 44E is disposed in the inner space of the high bending stiffness portion 22E.

In the variable stiffness device 10E, the high bending stiffness portion 22E always has high stiffness, so as to be relatively difficult to bend. The low bending stiffness portion 24E is easier to bend than the high bending stiffness portion 22E.

In the variable stiffness device 10E in the soft state shown in FIG. 6A, no current is supplied to the heater 70. Thus, the partially extending shape-memory pipe 44E is in the first phase, e.g., the martensitic phase, so as to be in the low stiffness state. In the variable stiffness device 10E in the soft state shown in FIG. 6A, the high bending stiffness portion 22E is relatively difficult to bend, and the low bending stiffness portion 24E is relatively easy to bend.

In the variable stiffness device 10E in the hard state shown in FIG. 6B, a current is supplied to the heater 70, and the heating element 72 disposed in the inner space of the partially extending shape-memory pipe 44E on the left side of FIG. 6B generates heat. The heat is efficiently transferred to the partially extending shape-memory pipe 44E. Thereby, the partially extending shape-memory pipe 44E on the left side of FIG. 6B is heated, so that the temperature thereof rises. In FIG. 6B, the heated partially extending shape-memory pipe 44E is shown shaded with dots. The heated partially extending shape-memory pipe 44E undergoes phase transformation, so as to transition in phase from the first phase, e.g., the martensitic phase, to the second phase, e.g., the austenitic phase. As a result, the heated partially extending shape-memory pipe 44E provides high stiffness to the portion of the soft pipe 54B between the two hard pipes 52B on the left side of FIG. 6B. In other words, the heated partially extending shape-memory pipe 44E causes the portion of the soft pipe 54B around the heated partially extending shape-memory pipe 44E to be difficult to bend. Thus, the portion 104 of the first elongated member 20E including the two hard pipes 52B on the left side of FIG. 6B and the portion of the soft pipe 54B between the two hard pipes 52B is more difficult to bend than when in the soft state shown in FIG. 6A.

In this way, it is possible to selectively cause a specific low bending stiffness portion 24E to be difficult to bend as compared with the soft state shown in FIG. 6A by supplying a current to the heater 70.

Immediately after the supply of current to the heater 70 is stopped, the heated partially extending shape-memory pipe 44E is still in the state of having heat upon heating, in the second phase, e.g., the austenitic phase, so as to be in the high stiffness state. Therefore, simply by stopping the supply of current to the heater 70, the variable stiffness device 10E in the hard state will not enter the soft state immediately.

In the present embodiment, when returning the variable stiffness device 10E in the hard state to the soft state, the although temperature decrease of the partially extending shape-memory pipe 44E by natural heat dissipation may be waited for, but preferably, instead, as shown in FIG. 6C, the second elongated member 30E is moved by the moving mechanism 90 along the longitudinal axis relative to the first elongated member 20E so that the partially extending shape-memory pipe 44E that has been heated by the heater 70 is disposed in the inner space of the high bending stiffness portion 22E. As a result, the spring 66E is now disposed at the low bending stiffness portion 24E where the heated partially extending shape-memory pipe 44E has been disposed. Thereby, that low bending stiffness portion 24E is easy to bend as compared with the hard state shown in FIG. 6B.

In the present embodiment, since the heated partially extending shape-memory pipe 44E is moved into the inner space of the high bending stiffness portion 22E when returning the variable stiffness device 10E in the hard state to the soft state, the variable stiffness device 10E can be returned to the soft state in a time shorter than the time required for waiting for the temperature decrease of the partially extending shape-memory pipe 44E by natural heat dissipation.

In this way, the variable stiffness device 10E can provide partially different stiffness to the flexible member in which it is installed. Specifically, the variable stiffness device 10E can provide different stiffness to the portion of the flexible member where the low bending stiffness portion 24E of the first elongated member 20E is disposed.

Advantageous Effect

In the variable stiffness device 10E of the present embodiment, by selectively changing the presence or absence of the supply of current to a specific heating element 72 of the heater 70, the stiffness of the low bending stiffness portion 24E corresponding to that heating element 72 can be changed. This allows providing partially different stiffness to the flexible member in which the variable stiffness device 10E is installed.

The heater 70 extends through the inner space of the partially extending shape-memory pipe 44E. Thus, the heating element 72 of the heater 70 is disposed adjacent to the partially extending shape-memory pipe 44E. For example, the heating element 72 is disposed in direct contact with the partially extending shape-memory pipe 44E. Accordingly, the heat generated by the heating element 72 is efficiently transferred to the partially extending shape-memory pipe 44E. Thereby, rapid phase transformation of the partially extending shape-memory pipe 44E from the first phase to the second phase is obtained. Thus, in the transition from the soft state to the hard state, the variable stiffness device 10E has high responsiveness.

In addition, since the heated partially extending shape-memory pipe 44E is moved into the inner space of the high bending stiffness portion 22E when returning the variable stiffness device 10E in the hard state to the soft state, the variable stiffness device 10E can be returned to the soft state in a time shorter than the time required for waiting for the temperature decrease of the partially extending shape-memory pipe 44E by natural heat dissipation. Thus, in the transition from the hard state to the soft state, the variable stiffness device 10E has high responsiveness.

The partially extending shape-memory pipes 44E are spaced apart from one another along the longitudinal direction. Thus, the volume of the partially extending shape-memory pipe 44E to be heated in order to harden the low bending stiffness portion 24E in the present embodiment is smaller than the volume of the full length extending shape-memory pipe 42A to be heated in order to harden the low bending stiffness portion 24A in the first embodiment. Therefore, in the transition from the soft state to the hard state, the variable stiffness device 10E of the present embodiment has higher responsiveness than the variable stiffness device 10A of the first embodiment.

Since the partially extending shape-memory pipes 44E are spaced apart from one another along the longitudinal direction, a partially extending shape-memory pipe 44E located next to the partially extending shape-memory pipe 44E to be heated is less likely to be undesirably heated.

Furthermore, the partially extending shape-memory pipe 44E of the present embodiment is shorter in length than the full length extending shape-memory pipe 42A of the first embodiment, so as to have excellent processability.

Modification of Fourth Embodiment

Figure 7:
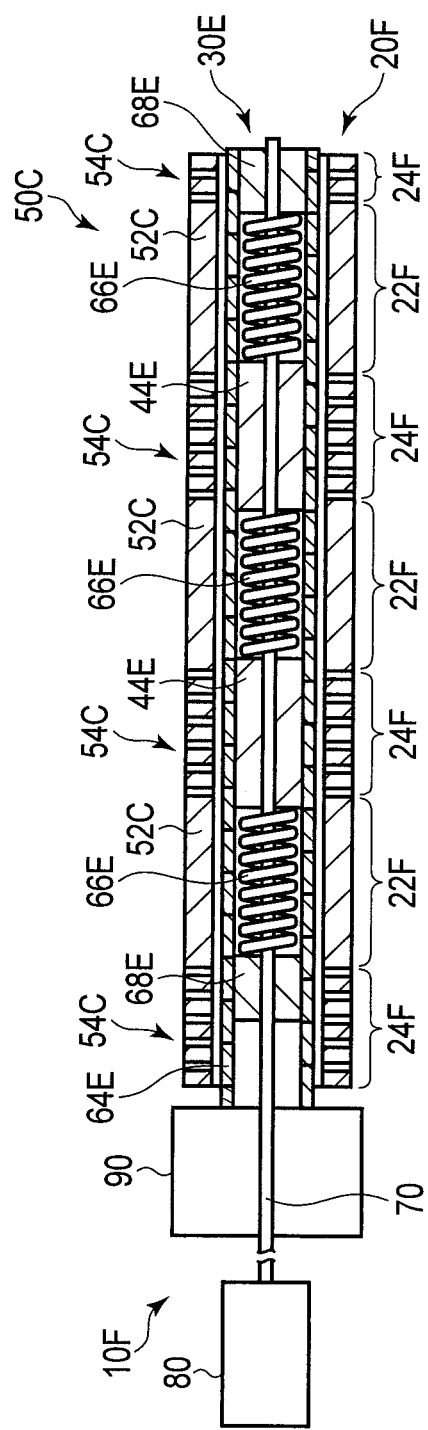
FIG. 7 shows a variable stiffness device according to a modification of the fourth embodiment.

FIG. 7 shows a variable stiffness device 10F according to a modification of the fourth embodiment. The variable stiffness device 10F has a configuration in which the first elongated member 20E in the variable stiffness device 10E is replaced with a first elongated member 20F.

As shown in FIG. 7, the variable stiffness device 10F includes the first elongated member 20F and the second elongated member 30E. The first elongated member 20F extends along the longitudinal axis. Similarly to the first elongated member 20F, the second elongated member 30E extends along the longitudinal axis, and is disposed adjacent to the first elongated member 20F. The first elongated member 20F and the second elongated member 30E are disposed so as to be relatively movable along the longitudinal axis.

Details of the second elongated member 30E (i.e., the shape-memory pipe 40E and the heater 70), the current supply unit 80, and the moving mechanism 90 are as described above.

The first elongated member 20F includes high bending stiffness portions 22F and low bending stiffness portions 24F. The high bending stiffness portions 22F and the low bending stiffness portions 24F are alternately arranged along the longitudinal axis of the first elongated member 20F. The high bending stiffness portion 22F has higher bending stiffness than that of the low bending stiffness portion 24F. Thus, the first elongated member 20F is relatively easy to bend at the portion of the low bending stiffness portion 24F, and is relatively difficult to bend at the portion of the high bending stiffness portion 22F.

Similarly to the first elongated member 20C in the modification of the second embodiment, the first elongated member 20F is constituted of the slitted hard pipe 50C. Namely, the configuration of the first elongated member 20F is the same as that of the first elongated member 20C in the second embodiment. Details of the first elongated member 20C or the slitted hard pipe 50C are as described in the second embodiment.

Accordingly, the high bending stiffness portion 22F is constituted of the non-slit portion 52C. In addition, the low bending stiffness portion 24E is constituted of the slit portion 54C.

The length of each partially extending shape-memory pipe 44E is longer than that of the low bending stiffness portion 24F where that partially extending shape-memory pipe 44E can be disposed, i.e., the slit portion 54C. The length of the partially extending shape-memory pipe 44E is also preferably shorter than that of the high stiffness portion 22F where that partially extending shape-memory pipe 44E can be disposed, i.e., the non-slit portion 52C.

Alternatively, the length of the portion of each partially extending shape-memory pipe 44E heated by the heater 70 is longer than that of the low bending stiffness portion 24F where that partially extending shape-memory pipe 44E can be disposed, i.e., the slit portion 54C, and is preferably shorter than that of the high bending stiffness portion 22F where that partially extending shape-memory pipe 44E can be disposed, i.e., the non-slit portion 52C.

The variable stiffness device 10F according to the present modification is the same as the variable stiffness device 10E except for the first elongated member 20F. Also, the first elongated member 20F is functionally the same as the first elongated member 20E. Therefore, the operation, etc. of the variable stiffness device 10F are the same as those of the variable stiffness device 10E according to the fourth embodiment.

The slitted hard pipe 50C constituting the first elongated member 20F according to the present modification is smaller than the pipe 50B constituting the first elongated member 20E according to the fourth embodiment. Thereby, the variable stiffness device 10F according to the present modification can be configured to be small.

Since the slitted hard pipe 50C is produced by processing a single hard pipe, the slitted hard pipe 50C has less influence of tolerance than the pipe 50B constituted of the soft pipe 54B and the hard pipes 52B. In addition, the slitted hard pipe 50C can be formed smaller than the pipe 50B. Thereby, the variable stiffness device 10F according to the present modification can be configured to be smaller than the variable stiffness device 10E according to the fourth embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A variable stiffness device comprising:
a first elongated member having a hollow shape and extending along a longitudinal axis; and
a second elongated member including a plurality of heaters, the second elongated member being disposed inside an inner circumference of the first elongated member, and extending in parallel to the first elongated member along the longitudinal axis,
the first elongated member including one or more high bending stiffness portions and a plurality of low bending stiffness portions, the one or more high bending stiffness portions and the plurality of low bending stiffness portions being alternately aligned along the longitudinal axis,
one of the first elongated member and the second elongated member including a shape-memory pipe, and
each of the plurality of heaters being spaced apart in an inner space of the shape-memory pipe such that a longitudinal position of each of the plurality of heaters corresponds with a longitudinal position of a low bending stiffness portion of the plurality of low bending stiffness portions, respectively, the plurality of heaters being configured to heat portions of the shape-memory pipe corresponding to the plurality of low bending stiffness portions to increase stiffness of the shape-memory pipe.
2. The variable stiffness device according to claim 1, wherein
the first elongated member includes the shape-memory pipe, the shape-memory pipe of comprises a full length extending shape-memory pipe continuously extending over substantially an entire length of the first elongated member,
the first elongated member also includes a hard pipe partially extending along the full length extending shape-memory pipe,
the hard pipe has higher bending stiffness than the full length extending shape-memory pipe,
a part of the full length extending shape-memory pipe comprises the plurality of low bending stiffness portions, and
the hard pipe comprises a part of the one or more high bending stiffness portions.

3. The variable stiffness device according to claim 2, wherein each of the plurality of heaters includes a heating element configured to heat the part of the full length extending shape-memory pipe corresponding to the low bending stiffness portion of the plurality of low bending stiffness portions.

4. The variable stiffness device according to claim 2, wherein
the first elongated member includes at least three hard pipes spaced apart from one another along the longitudinal axis,
each of the plurality of heaters includes a heating element, each of the heating elements being spaced apart from one another along the longitudinal axis,
each of the heating elements is disposed between two adjacent hard pipes, and
each of the hard pipes has higher bending stiffness than the full length extending shape-memory pipe.

5. The variable stiffness device according to claim 1, wherein
the first elongated member includes the shape-memory pipe,
the shape-memory pipe of comprises a partially extending shape-memory pipe partially extending along the longitudinal axis,
the first elongated member also includes a hard pipe connected to the partially extending shape-memory pipe,
the hard pipe has higher bending stiffness than the partially extending shape-memory pipe,
portions of the partially extending shape-memory pipe comprise the plurality of low bending stiffness portions, and
the hard pipe comprise a part of the one or more high bending stiffness portions.

6. The variable stiffness device according to claim 5, wherein the wherein the plurality of heaters each include a heating element configured to heat the partially extending shape-memory pipe.

7. The variable stiffness device according to claim 5, wherein
the shape-memory pipe comprises partially extending shape-memory pipes partially extending along the longitudinal axis,
the heating elements are spaced apart from one another along the longitudinal axis, and
the heating elements are disposed in inner spaces of the partially extending shape-memory pipes.

8. The variable stiffness device according to claim 1, wherein
the first elongated member comprises a pipe including the one or more high bending stiffness portions and the plurality of low bending stiffness portions,
the second elongated member includes the shape-memory pipe, and
the shape-memory pipe is disposed in an inner space of the pipe.

9. The variable stiffness device according to claim 8, wherein the shape-memory pipe comprises a full length extending shape-memory pipe continuously extending over substantially an entire length of the second elongated member.

10. The variable stiffness device according to claim 9, wherein the plurality of heaters include at least one heating element configured to heat portions of the full length extending shape-memory pipe corresponding to the plurality of low bending stiffness portions.

11. The variable stiffness device according to claim 10, further comprising a moving device configured to move the second elongated member along the longitudinal axis relative to the first elongated member so that a portion of the full length extending shape-memory pipe that will be heated by the plurality of heaters is disposed in an inner space corresponding to the plurality of low bending stiffness portions, and so that a portion of the full length extending shape-memory pipe that has been heated by the plurality of heaters is disposed in an inner space corresponding to the one or more high bending stiffness portions.

12. The variable stiffness device according to claim 8, wherein
the second elongated member includes a soft pipe continuously extending over substantially an entire length of the second elongated member,
the shape-memory pipe comprises a partially extending shape-memory pipe partially extending along the longitudinal axis, and
the partially extending shape-memory pipe is disposed in an inner space of the soft pipe.

13. The variable stiffness device according to claim 12, wherein the plurality of heaters include a heating element configured to heat the partially extending shape-memory pipe.

14. The variable stiffness device according to claim 12, wherein
the shape-memory pipe comprises partially extending shape-memory pipes partially extending along the longitudinal axis, and
the plurality of heaters include at least one heating element configured to heat the partially extending shape-memory pipes.

15. The variable stiffness device according to claim 12, further comprising a moving device configured to move the second elongated member along the longitudinal axis relative to the first elongated member so that the partially extending shape-memory pipe is disposed in an inner space corresponding to the plurality of low bending stiffness portions, and so that the partially extending shape-memory pipe is disposed in an inner space corresponding to the one or more high bending stiffness portions.

16. The variable stiffness device according to claim 8, wherein
the pipe in the first elongated member comprises a soft pipe continuously extending over substantially an entire length of the first elongated member and a hard pipe partially extending along the soft pipe,
a part of the soft pipe comprises the plurality of low bending stiffness portions, and
the hard pipe comprises a part of the one or more high bending stiffness portions.

17. The variable stiffness device according to claim 8, wherein the pipe in the first elongated member comprises a slitted hard pipe including slit portions and non-slit portions alternately aligned along the longitudinal axis, the slit portion comprises the plurality of low bending stiffness portions, and the non-slit portion comprises the one or more high bending stiffness portions.

18. A method of varying stiffness of a variable stiffness device, the variable stiffness device comprising:

a first elongated member having a hollow shape and extending along a longitudinal axis; and a second elongated member including a plurality of heaters, the second elongated member being disposed inside an inner circumference of the first elongated member, and extending in parallel to the first elongated member along the longitudinal axis, the first elongated member including one or more high bending stiffness portions and a plurality of low bending stiffness portions, the one or more high bending stiffness portions and the plurality of low bending stiffness portions being alternately aligned along the longitudinal axis, one of the first elongated member and the second elongated member including a shape-memory pipe, and each of the plurality of heaters being spaced apart in an inner space of the shape-memory pipe such that a longitudinal position of each of the plurality of heaters corresponds with a longitudinal position of a low bending stiffness portion of the plurality of low bending stiffness portions, respectively, the method comprising:

heating, by the plurality of heaters, portions of the shape-memory pipe corresponding to the plurality of low bending stiffness portions to increase bending stiffness of the shape-memory pipe; and lowering a temperature of the portions of the shape-memory pipe corresponding to the plurality of low bending stiffness portions to decrease the bending stiffness of the shape-memory pipe.

\* \* \* \* \*